(12) United States Patent
Papaioannou

(10) Patent No.: US 11,524,136 B2
(45) Date of Patent: Dec. 13, 2022

(54) NON-INVASIVE MEASUREMENT OF THE PITCH OF A BRAID

(71) Applicant: Biosense Webster (Israel) Ltd., Yokneam (IL)

(72) Inventor: Athanassios Papaioannou, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1024 days.

(21) Appl. No.: 16/231,846

(22) Filed: Dec. 24, 2018

(65) Prior Publication Data

US 2020/0197661 A1 Jun. 25, 2020

(51) Int. Cl.
*A61M 25/01* (2006.01)
*A61M 25/00* (2006.01)
(Continued)

(52) U.S. Cl.
CPC .... *A61M 25/0012* (2013.01); *A61M 25/0053* (2013.01); *G01N 21/41* (2013.01);
(Continued)

(58) Field of Classification Search
CPC ........... G01N 21/9081; G01N 27/4146; G01N 21/952; G01N 21/95; G01N 21/4795; G01N 21/9054; G01N 2021/8848; G01N 2021/8861; G01N 2021/8874; G01N 2021/8887; G01N 2021/9563; G01N 21/8806; G01N 21/8851; G01N 21/8915; G01N 21/8983; G01N 21/9515; G01N 21/954; G01N 21/956; G02B 1/14; G02B 23/2476; G02B 5/0268; G02B 6/02; G02B 5/0215; G02B 6/02033; G02B 6/0045; G02B 6/4486; G02B 6/036; G01B 11/24; G01B 11/0625; G01B 11/06; G01B 11/165; G01B 9/02091; G01B 11/046; G01B 15/025; G01B 17/025; G01B 11/0616; G01B 7/18; G01B 11/0683; G01B 11/16; G01B 9/0205; G01B 2210/58; G01B 11/18; G01B 15/02; G01B 7/22; G01B 11/00;
(Continued)

(56) References Cited

U.S. PATENT DOCUMENTS 2,513,349 A * 7/1950 Nase ........................ H01J 19/46
250/221
5,406,374 A * 4/1995 Shimada ................. G01M 11/37
356/73.1
(Continued)

FOREIGN PATENT DOCUMENTS

CN 112229842 A * 1/2021
DE 19613175 A1 * 10/1997 ............. G01B 5/204
(Continued)

*Primary Examiner* — Michael P Stafira
(74) *Attorney, Agent, or Firm* — Frost Brown Todd LLC

(57) ABSTRACT

Described embodiments include a system for inspecting a tubular device that includes an outer surface and a spatially-periodic supporting structure beneath the outer surface. The system includes an imaging device, configured to acquire an image of a reflection of light from the outer surface, and a processor, configured to ascertain a spatial frequency of the supporting structure by processing the image. Other embodiments are also described.

20 Claims, 4 Drawing Sheets

(51) Int. Cl.
*G01N 21/41* (2006.01)
*G01N 21/17* (2006.01)

(52) U.S. Cl.
CPC .............. *G01N 2021/1765* (2013.01); *G01N 2021/418* (2013.01)

(58) Field of Classification Search
CPC ... G01B 11/0633; G01B 11/14; G01B 11/254; G01B 11/255; G01B 17/00; G01B 21/08; G01B 5/02; G01B 7/085; G01B 9/02; G01B 11/2425; G01B 11/2433; G01B 11/245; G01B 5/204; G01B 11/002; G01B 11/022; G01B 5/008; G01B 11/26; G01B 5/0002; G01B 5/163; G01B 11/03; G01B 11/08; G01B 11/105; G01B 11/25; G01B 11/2513; G01B 11/2531; G01B 21/04; G01B 21/047; G01B 5/012; G01B 7/008; G01B 9/0201; G01B 9/02048; A61M 5/178; A61M 5/3286; A61M 5/3291; D05B 19/14; D05B 19/16; D05B 19/085; D05B 19/10; D05B 19/105; D05B 19/12; D05B 21/00; D05B 27/08; D05B 35/102; D05B 81/00; D05B 19/08; D05B 35/066; D05B 35/12; D05B 69/36; G06T 1/0014; G06T 2207/20081; G06T 7/001; G06T 2207/10004; G06T 2207/30141; G06T 7/0004; D05D 2205/02; D05D 2205/12; D05D 2205/18; D05D 2207/00
See application file for complete search history.

(56) References Cited

U.S. PATENT DOCUMENTS

| | | | |
|---|---|---|---|
| 7,020,324 B2 * | 3/2006 | Freifeld | G01N 21/952 382/152 |
| 2007/0167801 A1 | 7/2007 | Webler et al. | |
| 2010/0256601 A1 | 10/2010 | Lippert et al. | |
| 2013/0050830 A1 * | 2/2013 | Sterud | G01N 21/9515 359/599 |
| 2020/0197661 A1 * | 6/2020 | Papaioannou | G01N 21/41 |

FOREIGN PATENT DOCUMENTS

| | | | | |
|---|---|---|---|---|
| DE | 102015016416 A1 * | 6/2016 | ............... | D04C 3/48 |
| EP | 2392895 A1 * | 12/2011 | ............. | A61B 6/027 |
| EP | 2439488 A1 * | 4/2012 | ............. | G01B 11/00 |
| EP | 3673785 B1 * | 8/2021 | ......... | A61B 1/00057 |
| JP | 2010000693 A * | 1/2010 | | |
| JP | 2010197107 A * | 9/2010 | | |
| JP | 2011053202 A * | 3/2011 | | |
| JP | 2014062835 A * | 4/2014 | | |
| KR | 101415005 B1 * | 7/2014 | ......... | A61B 1/00057 |

* cited by examiner

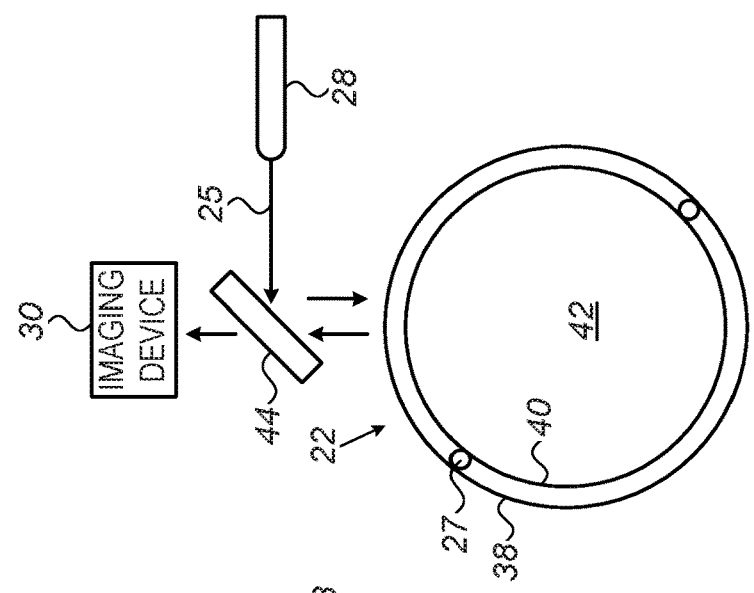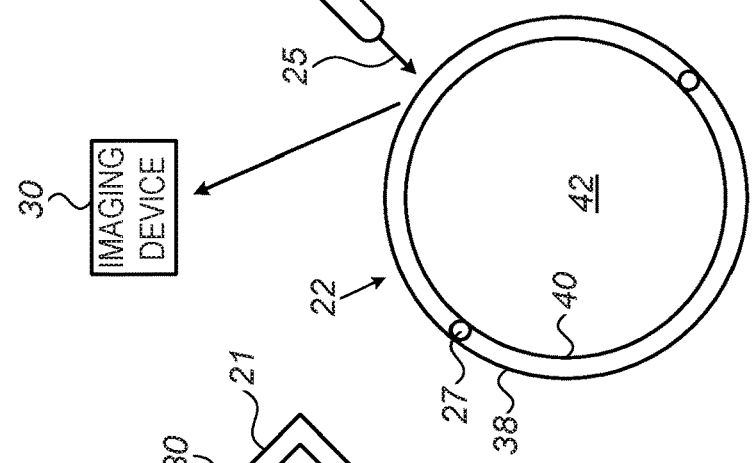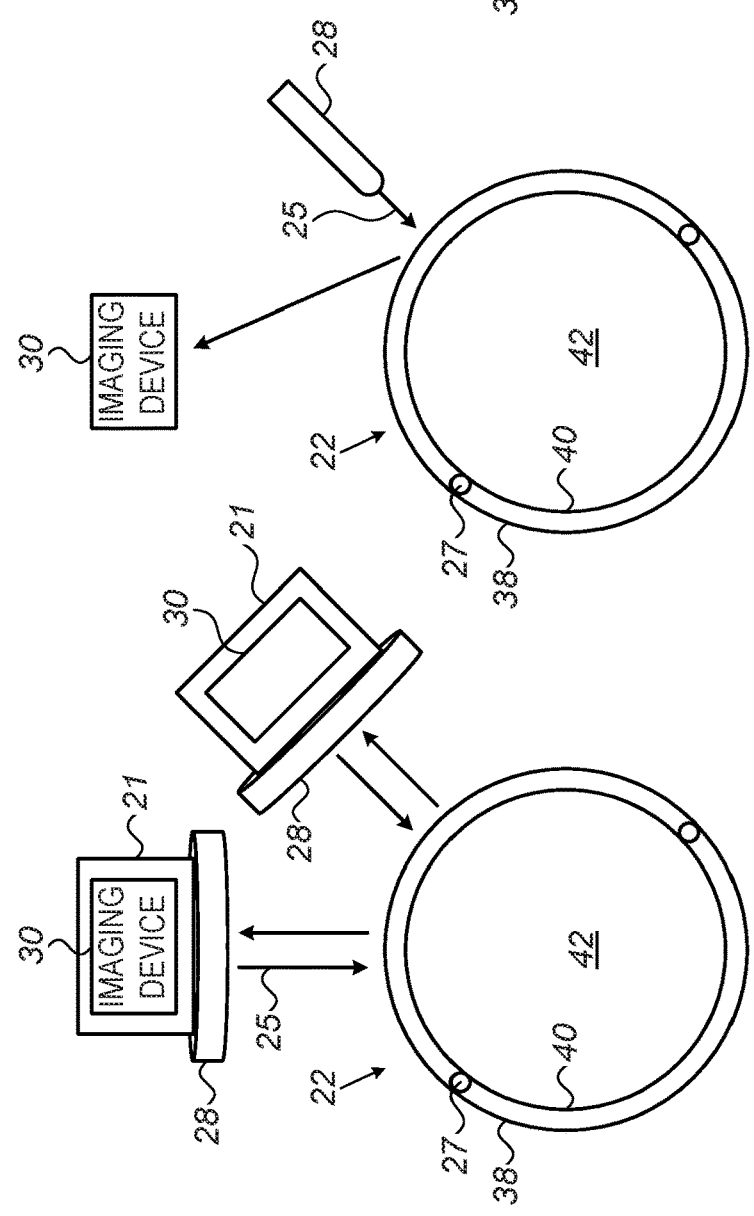

NON-INVASIVE MEASUREMENT OF THE PITCH OF A BRAID

FIELD OF THE INVENTION

The present invention relates generally to the manufacture of braided structures, such as braided extrusions for use in intrabody catheter shafts and other tubular devices.

BACKGROUND

Some tubular devices, such as the shafts of intrabody catheters, comprise an inner tube and an outer tube, with a braided skeletal structure positioned between the two tubes. The braid imparts stability, along with other mechanical properties, to the catheter. The pitch of the braid is typically measured in units of picks per inch (PPI).

SUMMARY OF THE INVENTION

There is provided, in accordance with some embodiments of the present invention, a system for inspecting a tubular device that includes an outer surface and a spatially-periodic supporting structure beneath the outer surface. The system includes an imaging device, configured to acquire an image of a reflection of light from the outer surface, and a processor, configured to ascertain a spatial frequency of the supporting structure by processing the image.

In some embodiments, the system further includes a light source, configured to illuminate the outer surface with the light so as to generate the reflection.

In some embodiments, the processor is further configured to, in response to the spatial frequency being different from a target spatial frequency, control a manufacturing of the tubular device so as to bring the spatial frequency into accordance with the target spatial frequency.

In some embodiments, the supporting structure is selected from the group of supporting structures consisting of: a coil, and a braid.

In some embodiments, the reflection is shaped to define a sinusoid, and the processor is configured to ascertain the spatial frequency of the supporting structure based on a frequency of the sinusoid.

In some embodiments, the processor is further configured to, prior to processing the image:
compare a parameter of the sinusoid, as exhibited in the image, to the parameter as exhibited in another image, and
select the image, but not the other image, for the processing, in response to the comparison.

In some embodiments, the parameter includes a peak-to-peak amplitude of the sinusoid.

In some embodiments, the parameter includes an energy of a dominant frequency of the sinusoid.

In some embodiments, the spatial frequency of the supporting structure is a first spatial frequency, and the processor is configured to ascertain the first spatial frequency based on a second spatial frequency of an intensity of the reflection.

There is further provided, in accordance with some embodiments of the present invention, a method that includes, using a light source, illuminating an outer surface of a tubular device with light, the tubular device including a spatially-periodic supporting structure beneath the outer surface. The method further includes, while illuminating the outer surface, using an imaging device, acquiring an image of a reflection of the light from the outer surface. The method further includes, by processing the image, ascertaining a spatial frequency of the supporting structure.

In some embodiments, illuminating the outer surface includes illuminating the outer surface while the tubular device is being manufactured.

In some embodiments, the supporting structure includes at least two coils that are braided with one another, and illuminating the outer surface includes illuminating the outer surface such that peaks of the sinusoid are located at respective crossings of the coils.

There is further provided, in accordance with some embodiments of the present invention, a computer software product including a tangible non-transitory computer-readable medium in which program instructions are stored. The instructions, when read by a processor, cause the processor to receive an image of a reflection of light from an outer surface of a tubular device that includes a spatially-periodic supporting structure beneath the outer surface, and to ascertain a spatial frequency of the supporting structure by processing the image.

The present invention will be more fully understood from the following detailed description of embodiments thereof, taken together with the drawings, in which:

BRIEF DESCRIPTION OF THE DRAWINGS

FIGS. 2A-C schematically illustrate various alternate configurations of the system of FIG. 1, in accordance with some embodiments of the present invention;

DETAILED DESCRIPTION OF EMBODIMENTS

Overview

Figure 1:
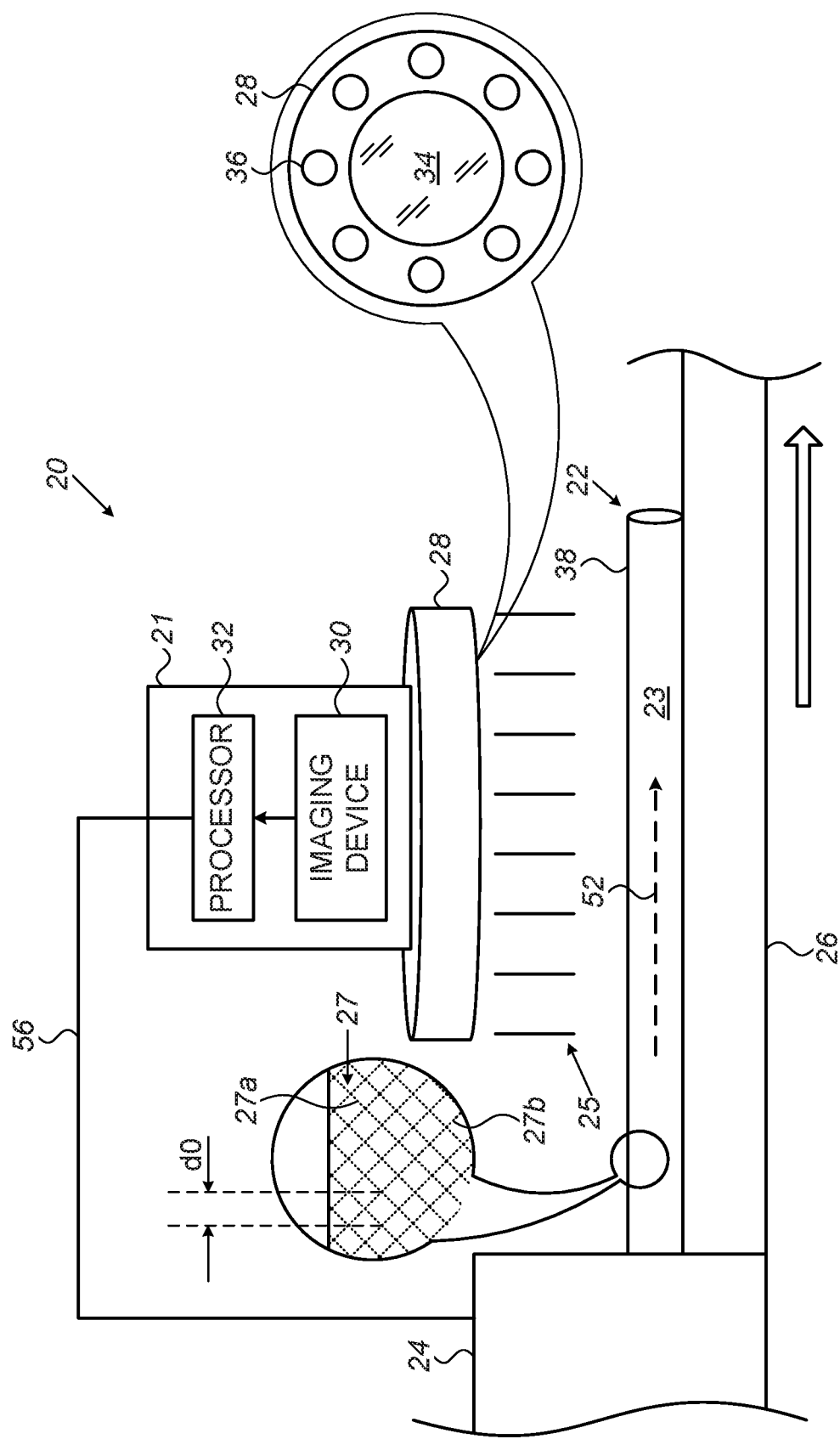
FIG. 1 is a schematic illustration of a system for inspecting a catheter shaft during the manufacture thereof, in accordance with some embodiments of the present invention.

For a tubular device that comprises a supporting braid, as described above in the Background, the pitch of the braid may affect the mechanical properties of the device. It is therefore important to verify, during the manufacturing process, that the desired pitch of the braid is attained. One method for doing so is to cut away part of the outer tube of the device, and to then measure the pitch of the braid. However, this method involves interruptions to the manufacturing process, along with wasted materials. These disadvantages are especially pronounced in cases in which the pitch of the braid is required to change along the length of the device.

To address this challenge, embodiments of the present invention use a non-destructive, non-invasive method of measuring the braid of the device, without interrupting the manufacturing process. This method takes advantage of the fact that the braid typically causes the outer tube of the device to bulge slightly outward, such that the outer surface of the device reflects light in a manner that depends on the pitch of the underlying braid. In particular, per the techniques disclosed herein, the surface of the device is illuminated while the device is in the process of being manufactured. Using a suitable imaging device, an image of the reflection of the light from the surface is captured. Subsequently, by processing the image, the pitch of the underlying braid is ascertained.

In some cases, the position of the reflection in the image may vary periodically (e.g., sinusoidally), in that the reflection may include a series of alternating positive and negative peaks, the positive peaks corresponding to the points at which the braid passes beneath the surface. Alternatively or additionally, the intensity (or "brightness") of the reflection may vary periodically (e.g., sinusoidally), whereby the intensity attains its maximum value at the points at which the braid passes beneath the surface. (The type of periodicity that is exhibited generally depends on various factors, such as the type of light source that is used, the position of the light source relative to the device, and the position of the imaging device relative to the device.) Since each of these types of periodicity indicates the pitch of the underlying braid, the processing of the image may include the identification of one or both of these types of periodicity.

For example, the processor may calculate the distance between the peaks in the reflection, and/or between the peaks in the intensity of the reflection, so that the pitch of the underlying braid may be ascertained. Alternatively, the processor may carry out a Fast Fourier Transform (FFT) of the position or intensity of the reflection, and the pitch may then be ascertained directly from the transform.

Advantageously, the techniques described herein are non-destructive and cost-effective, and allow the braid to be inspected in real-time, as the device is manufactured, without interrupting the manufacturing process. Moreover, the techniques described herein greatly facilitate the inspection of more complex braid types, such as those with a variable (e.g., stepped) pitch. In the event that a deviation from the specifications is found, the manufacturing process may be adjusted in real-time, so as to salvage the device. Thus, the duration and cost of the manufacturing process may be reduced.

Furthermore, the techniques described herein may be applied to most types of tubular devices, including those with properties that would inhibit the use of other inspection techniques. For example, the techniques described herein may be applied even to tubular devices whose outer tubes are opaque to visible light and/or x-rays, e.g., due to the thickness of the outer tube (e.g., by virtue of the outer tube comprising multiple layers of material), and/or due to impregnation of the outer tube with opaque materials such as colorants, lubricious agents, or radiopaque materials such as tungsten.

Although the description below generally focuses on the manufacture of an intrabody catheter shaft, it is noted that the techniques described herein may be similarly applied to any other suitable tubular device that comprises a supporting braid. Examples of such devices include intrabody probe shafts, sheaths and other introducers for introducing intrabody devices into mammalian bodies, garden hoses, and other flexible conduits for the transport of liquids or gasses.

System Description

Reference is initially made to FIG. 1, which is a schematic illustration of a system 20 for inspecting a catheter shaft 22 during the manufacture thereof, in accordance with some embodiments of the present invention.

FIG. 1 depicts the manufacture of catheter shaft 22 by manufacturing apparatus 24. In the particular example shown, as raw materials pass through apparatus 24, the apparatus forms the catheter shaft from the raw materials. For example, apparatus 24 may comprise one or more extrusion dies, and catheter shaft 22 may be formed by extrusion. (In such a case, the catheter shaft itself may be referred to as a "braided extrusion," or simply as an "extrusion.") Alternatively, the techniques described herein may be applied to any other suitable type of manufacturing process, such as an additive manufacturing process.

Catheter shaft 22 comprises an outer tube 38, which is typically made from a polymer. Outer tube 38 comprises an outer surface 23. Underneath outer tube 38, catheter shaft 22 comprises a supporting structure (or "skeletal structure") 27. Underneath structure 27, catheter shaft 22 comprises an inner tube, which is not shown in FIG. 1.

In some cases, structure 27 comprises a braid. One type of braid, shown in FIG. 1, may be formed by winding a first coil 27a and a second coil 27b over the inner tube of the catheter shaft with the same pitch (alternatively referred to herein as a "spatial frequency") but with different orientations. For example, one of the coils may be oriented (e.g., at a 45° angle) toward the distal end of the catheter shaft, while the other coil may be oriented (e.g., at a 45° angle) toward the proximal end of the catheter shaft. In this case, the pitch of the braid is the inverse of the distance d0 between successive crossing of the coils, d0 being measured along the longitudinal axis 52 of the catheter shaft. Other types of braids may be formed using any suitable combination of coils, loops, and/or straight wires, which may be oriented in any suitable way.

Alternatively, structure 27 may comprise a single coil wound over the inner tube of the catheter shaft. In this case, the spatial frequency of the structure is the inverse of the distance between successive windings of the coil, this distance being measured along longitudinal axis 52.

In general, each coil in supporting structure 27 may comprise any suitable material, such as stainless steel, Nitinol, a polymer (e.g., a liquid-crystal polymer or polyether ether ketone), glass, and/or carbon fiber. The cross section of each coil may have any suitable shape, such as a circular or rectangular shape.

System 20 comprises an inspection unit 21. Upon exiting apparatus 24, the catheter shaft is carried, by a track 26, under inspection unit 21. (This movement is toward the right of the figure, as indicated by the right-pointing arrow at the bottom of the figure.) The speed at which track 26 moves—referred to as the "line speed"—may be, for example, between 8 and 70 cm/s.

Unit 21 comprises a light source 28 and at least one imaging device 30, comprising, for example, an imaging lens and an imaging sensor, such as a charged coupled device (CCD) or complementary metal-oxide-semiconductor (CMOS). As the catheter shaft passes underneath the unit, light source 28 illuminates outer surface 23 of the catheter shaft with light 25, such that light 25 is reflected by the outer surface through the imaging lens and onto the imaging sensor of imaging device 30. While the catheter shaft is illuminated, imaging device 30 acquires images of the reflection.

As further described below with reference to FIGS. 3-4, the reflection does not appear as a uniform, straight line, due to the presence of structure 27 beneath the outer surface. In particular, structure 27 causes outer surface 23 to be uneven, in that the portions of outer surface 23 that lie directly over the structure are raised, relative to the other portions of the outer surface. Hence, the reflection includes alternating positive and negative peaks, and/or varies periodically in its intensity.

System 20 further comprises a processor 32, which may be disposed within unit 21 or remotely therefrom. Processor 32 may be connected to imaging device 30 over any suitable wired or wireless interface, such that the images acquired by the imaging device are communicated to processor 32 over the interface. As described in further detail below with reference to FIGS. 3-4, processor 32 processes the images, such as to ascertain the pitch of the supporting structure from the reflection of light 25 in the image.

In response to ascertaining that the pitch is different from a target pitch that is specified in the relevant manufacturing specifications, processor 32 may control the manufacturing of the catheter shaft such as to bring the pitch into accordance with the target pitch. (In other words, processor 32 may provide feedback for a closed control loop for controlling the pitch.) For example, the processor may adjust the temperature, pressure, and/or tension applied to the raw materials by apparatus 24, and/or the line speed, such as to correct the pitch.

To facilitate this control functionality, processor 32 may be connected to manufacturing apparatus 24 over any suitable wireless or wired communication interface 56. For example, the processor may be connected to a controller belonging to manufacturing apparatus 24, such that the processor may instruct the controller to adjust any relevant manufacturing parameters.

Typically, the catheter shaft is imaged at a rate that is sufficient for acquiring at least one image of every portion of the shaft. (In general, the minimum sufficient rate is a function of the line speed and of the size of the field of view of the imaging device.) In some embodiments, the images are acquired at a rate of at least 15, 30, or 60 frames per second, such that, typically, multiple images of each portion of the shaft are acquired.

In some embodiments, the functionality of processor 32, as described herein, is implemented solely in hardware, e.g., using one or more Application-Specific Integrated Circuits (ASICs) or Field-Programmable Gate Arrays (FPGAs). In other embodiments, the functionality of processor 32 is implemented at least partly in software. For example, in some embodiments, processor 32 may be embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

In the particular embodiment shown, light source 28 comprises a set of light emitting diodes (LEDs) 36 arranged circularly around a central transparent window 34, behind which lies the imaging lens of imaging device 30. LEDs 36 may illuminate catheter shaft 22 simultaneously or in sequence, as further described below. As the LEDs illuminate the catheter shaft, the reflected light passes through window 34 to the imaging device.

More generally, system 20 may comprise one or more light sources and one or more imaging devices, which may be disposed in any suitable configuration. Each light source may comprise any suitable number of light emitters (e.g., LEDs, lasers, fluorescent bulbs, incandescent bulbs, and/or halogen bulbs), which may be arranged in any suitable configuration (e.g., a circular or linear configuration). The one or more light beams emitted by each light source may have any suitable shape (e.g., a circular or linear shape). Hence, any suitable pattern of coherent or incoherent illumination may be obtained. Furthermore, the light emitted by each of the light sources may have any suitable frequency, or combination of frequencies, within the visible or invisible portion of the electromagnetic spectrum (provided that the imaging devices are configured to image these frequencies).

In some embodiments, system 20 comprises a mobile phone, which comprises the aforementioned light source, imaging device, and processor. Alternatively or additionally, system 20 may comprise additional optical elements, such as additional lenses or beam splitters, which facilitate the illumination and imaging functionality described herein.

For various alternate configurations of system 20 in accordance with some embodiments of the present invention, reference is now made to FIGS. 2A-C. Each of FIGS. 2A-C shows a transverse cross-section through catheter shaft 22, along with various components of system 20. (For simplicity, processor 32 is omitted from FIGS. 2A-C.) The transverse cross-section reveals outer tube 38 (comprising outer surface 23), an inner tube 40, a catheter shaft lumen 42 enclosed by inner tube 40, and supporting structure 27, disposed between outer tube 38 and inner tube 40.

In FIG. 2A, system 20 comprises multiple inspection units 21, each of which provides coaxial illumination and imaging as in FIG. 1. In other words, each inspection unit illuminates the catheter shaft and receives the reflected light from the catheter shaft along a common axis. The inspection units are disposed at different respective angles with respect to the catheter shaft. In some embodiments, the inspection units image the catheter shaft at the same frequency (i.e., at the same number of images per second), in phase with each other. In other embodiments, the inspection units image the catheter shaft at different frequencies, or at the same frequency but with different phases. In any case, each imaging device typically images the catheter shaft at a rate that is sufficient for acquiring at least one image of every portion of the shaft, as described above with reference to FIG. 1.

Typically, a single processor 32, disposed within one of the imaging units or remotely therefrom, processes the images acquired by the imaging devices. In the event that multiple images of a single portion of the catheter shaft are acquired, at the same time, from different respective angles, processor 32 may use the multiple images to obtain a more accurate estimate of the spatial frequency of the underlying supporting structure; for example, the processor may average the spatial frequency across the images. Alternatively, as further described below with reference to FIGS. 3-4, the processor may select one or more images that show a more indicative reflection than the other images, and use only the selected images to ascertain the spatial frequency of the supporting structure.

In FIG. 2B, light source 28 and imaging device 30 are disposed at different respective angles with respect to the catheter shaft, such that system 20 provides off-axis illumination and imaging. (In other words, the illumination is delivered along a first axis, while the reflected light is received along a second, different axis.) In some cases, this off-axis configuration may provide a more indicative pattern of reflection, relative to a coaxial configuration.

The embodiment of FIG. 2B may further include one or more other light sources that illuminate the catheter shaft from other positions. The reflection of the light beams from these light sources may be imaged by one or more other coaxial or off-axis imaging devices, and/or by the same imaging device. Similarly, a single light source may be "shared" by multiple imaging devices, in that the reflection generated by the light source may be imaged by the devices from multiple different positions. As described above with reference to FIG. 2A, respective images may be acquired by the multiple imaging devices at the same time, or at different times. In the event that the images are acquired at the same time, the processor may select some or all of the images for use in ascertaining the spatial frequency of the supporting structure.

In FIG. 2C, as in FIG. 2B, light source 28 and imaging device 30 are disposed at different respective angles with respect to the catheter shaft. However, system 20 nonetheless provides coaxial illumination and imaging, by virtue of a beam splitter 44. The components shown in FIG. 2C may be combined with any number of other light sources, imaging devices, and/or other optical components, arranged in any suitable configuration.

Ascertaining the Spatial Frequency

Figure 3:
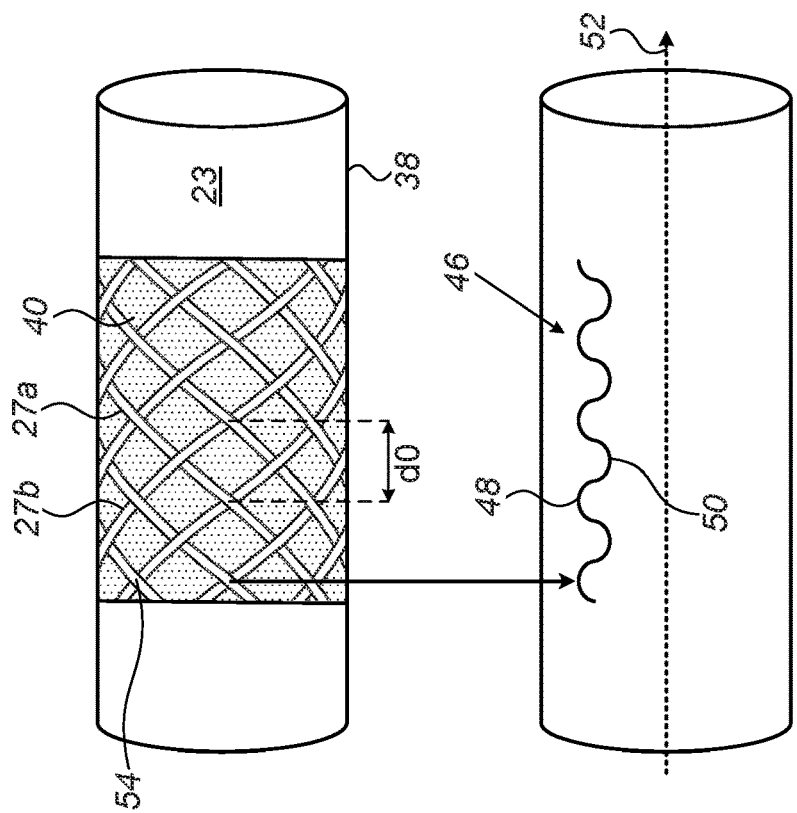

Reference is now made to FIG. 3, which is a schematic illustration of a method for ascertaining the spatial frequency of supporting structure 27, in accordance with some embodiments of the present invention.

At the top of FIG. 3, a portion of outer tube 38 is removed for illustration purposes, such as to show the spatially-periodic supporting structure underneath. In the particular example shown, as in FIG. 1, the supporting structure comprises a braid, comprising two coils wound around inner tube 40 at the same pitch but with opposite orientations.

As described above with reference to FIG. 1, the supporting structure causes unevenness in outer surface 23 of outer tube 38, such that the reflection 46 of light from the outer surface may exhibit certain non-uniformities. For example, as shown in the bottom portion of FIG. 3, the shape of reflection 46 may vary periodically along axis 52. For example, the reflection may be shaped to define a sinusoid (or any approximation to a sinusoid) having alternating positive peaks 48 and negative peaks 50, whereby positive peaks 48 are attained at the points of maximum outward bulging of outer surface 23, while negative peaks 50 correspond to the points of minimal outward bulging. In this case, the spatial frequency of the supporting structure may be ascertained based on the frequency of the sinusoid.

For example, after detecting the sinusoid (e.g., by applying a color filter and/or brightness filter to the image), the processor may compute the spatial frequency of the braid by (i) detecting the positive peaks of the sinusoid, (ii) computing the distance in pixels between a pair of successive positive peaks, or the average of this distance over multiple such pairs, (iii) scaling the inter-peak distance in accordance with the size of the field of view (FOV) of the imaging device, such as to obtain the real-world distance between the positive peaks, and (iv) computing the inverse of the real-world distance. Alternatively, an FFT of the sinusoid may be computed, and the dominant frequency of the FFT may then be identified. Subsequently, the spatial frequency of the braid may be computed by scaling the dominant frequency in accordance with the size (in pixels) of the FOV and the magnification factor of the imaging lens. (Prior to the imaging, a calibration procedure may be performed, so as to learn the respective scale factors for different magnification factors.)

Figure 4:
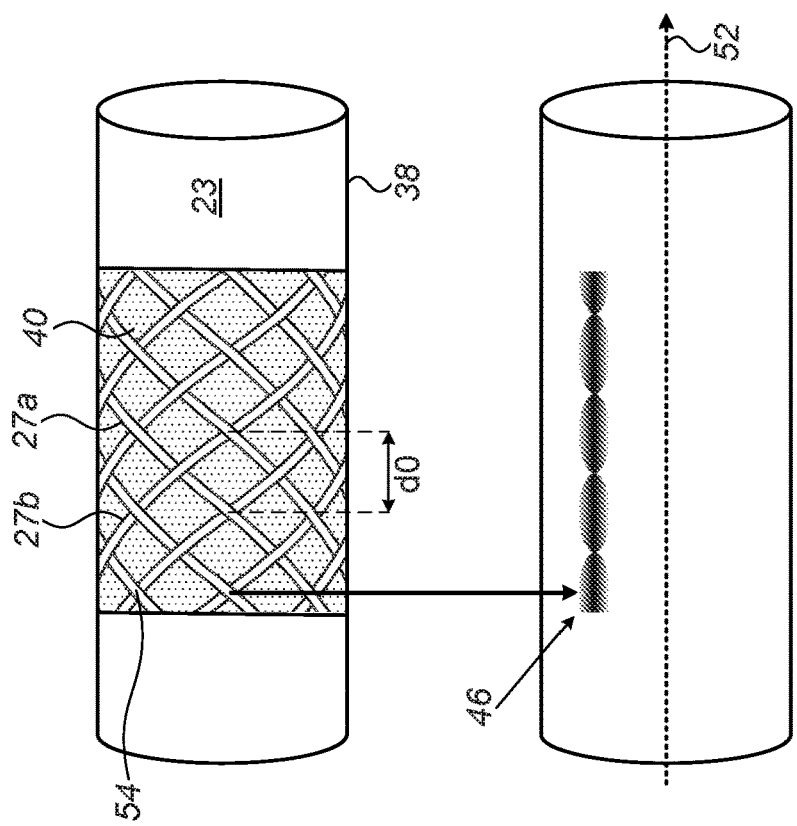
FIGS. 3-4 are schematic illustrations of methods for ascertaining the spatial frequency of a supporting structure, in accordance with some embodiments of the present invention.

Reference is now made to FIG. 4, which is a schematic illustration of another method for ascertaining the spatial frequency of supporting structure 27, in accordance with some embodiments of the present invention.

In some cases, alternatively or additionally to having a periodic shape, reflection 46 exhibits a spatially-periodic intensity, whereby the intensity is highest directly above the supporting structure. Hence, the spatial frequency of the supporting structure may be ascertained based on the spatial frequency of the reflection. For example, the processor may derive, from the image, a periodic function B(x) that describes the brightness of the reflection in the image, x being the distance along longitudinal axis 52. Subsequently, the processor may calculate the spatial frequency of the supporting structure by applying the above-described peak detection technique or FFT technique to B(x).

In some embodiments, processor 32 applies a software-implemented color filter to each image, prior to processing the image as described above with reference to FIGS. 3-4. Such a filter may, for example, filter out the color of outer tube 38, so as to increase the contrast between reflection 46 and the surrounding pixels. Alternatively or additionally, a physical color filter may filter the light received by imaging device 30.

Example Image-Processing Techniques

One example of the FFT computation referred to above includes use of MATLAB® to perform a two-dimensional FFT. For example, to process each images of the catheter shaft, the MATLAB® function "fft2" may be called, and the pitch of the braid may then be derived from the frequency at which the FFT attains its maximum value.

Figure 5:
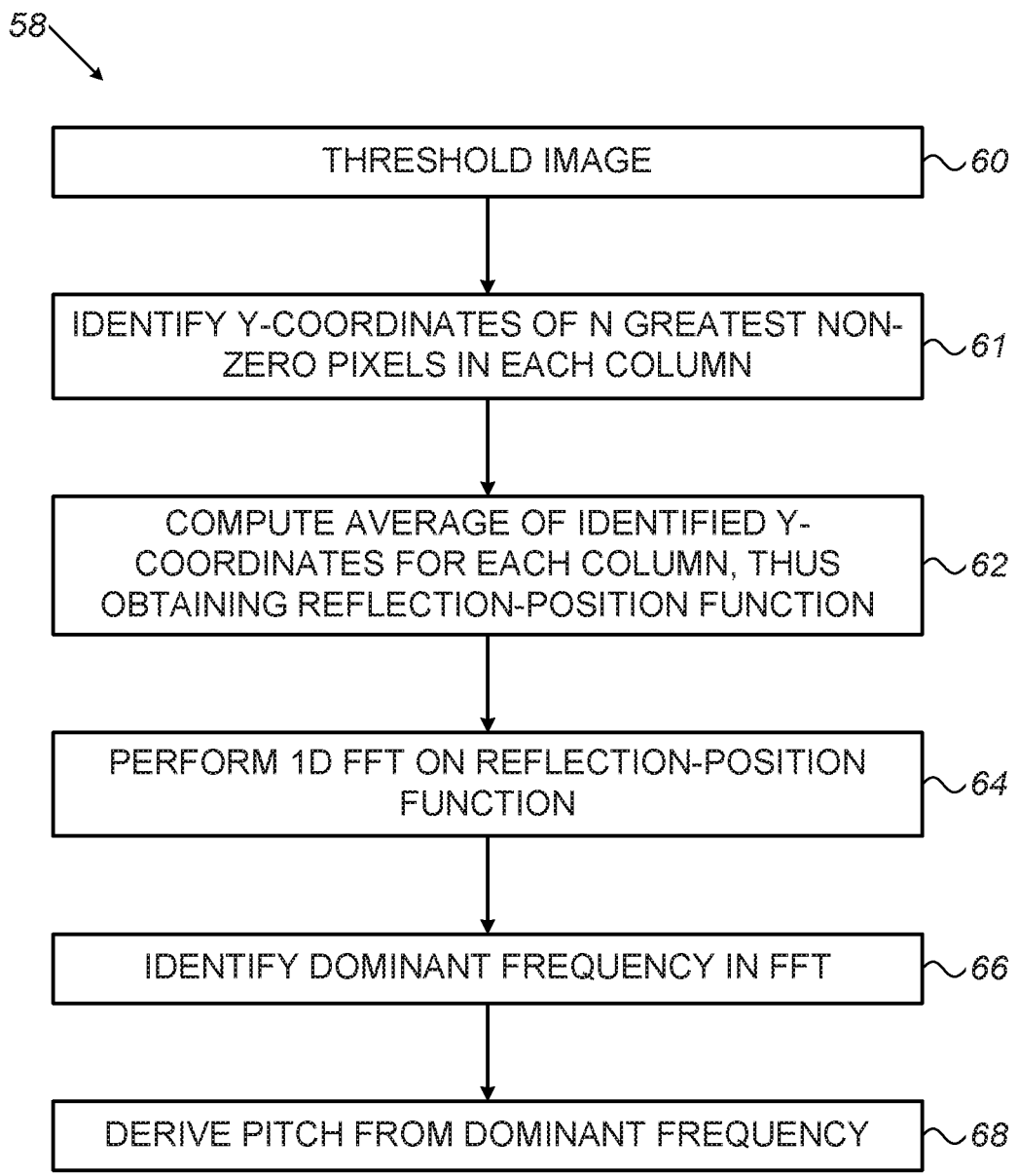
FIG. 5 is a flow diagram for a method for identifying the pitch of a braid, in accordance with some embodiments of the present invention.

Another computational approach, which utilizes a one-dimensional FFT, is illustrated in FIG. 5, which is a flow diagram for a method 58 for identifying the pitch of a braid, in accordance with some embodiments of the present invention.

The algorithm 58 begins with a thresholding step 60, at which processor 32 applies a suitable threshold to the image, setting any pixels whose value is less than the threshold to zero. In general, the threshold that is used is the minimum brightness value that the reflection is expected to attain in the image. (This thresholding operation was referred to above as the application of a "brightness filter" to the image.). One skilled in the art would be able to utilize algorithm 58 to generate suitable computer codes to perform the processing of the image.

Next, at a coordinates-identifying step 61, for any suitable integer N (e.g., any integer between one and ten), the processor identifies the respective y-coordinates of the N greatest non-zero pixels in each column of the image, for those columns that contain at least N non-zero pixels. (The MATLAB® function "find" may be used for this purpose.) Subsequently, at an average-computing step 62, the processor computes, for each column for which the aforementioned y-coordinates were identified, the average of the identified y-coordinates. The processor thus obtains a reflection-position function, which associates an average y-coordinate, representing the vertical position of the reflection, with each x-coordinate along the length of the reflection.

Next, the processor performs a one-dimensional FFT on the reflection-position function, at an FFT-performing step 64. (The MATLAB® function "fft" may be used for this purpose.) Subsequently, at a dominant-frequency-identifying step 66, the processor identifies the dominant frequency in the FFT. Finally, at a pitch-deriving step 68, the processor derives the pitch of the braid from the dominant frequency, e.g., by scaling the dominant frequency in accordance with the size of the FOV and the magnification factor of the imaging lens.

Although FIG. 5 assumes that the reflection has a horizontal orientation in the image, it is noted that method 58 may be similarly applied to a reflection having a vertical orientation, mutatis mutandis. Similarly, although FIG. 5 assumes that the pitch is derived from the periodically-varying position of the reflection in the image, it is noted that method 58 may be similarly used to derive the pitch of the braid from the periodically-varying brightness of the image, mutatis mutandis.

Selective Processing

In some embodiments, multiple images, which vary from each other in the position and/or shape of the reflection that is shown, are acquired at approximately the same time, e.g., such that the last image is acquired within 1-100 (e.g., within 5-50) milliseconds of the first image. Subsequently, the processor identifies at least one of these images as being more indicative of the spatial frequency of the supporting structure than the other images. The processor therefore selects the identified image—without selecting the other images—for processing. Alternatively or additionally, the processor may select, for processing, one of several reflections that are shown in an image, without selecting the other reflections.

Advantageously, this technique may facilitate estimating the pitch of the supporting structure with greater accuracy. For example, in some cases, for a braid with crossed-over coils as shown in FIGS. 3-4, the pitch may be estimated with greatest accuracy when the reflection is aligned with crossings 54. Hence, multiple images, which show reflections at different respective positions along the circumference of the catheter shaft, may be acquired. Subsequently, the processor may select the image in which the reflection appears to be most closely aligned with crossings 54. Alternatively, a single image, which shows multiple reflections at different respective positions along the circumference of the catheter shaft, may be acquired, and the processor may then select the reflection that appears to be most closely aligned with crossings 54.

In some embodiments, to facilitate performing this technique, light source 28 is configured to illuminate the catheter shaft at various different positions along the circumference of the shaft. For example, the circular arrangement of LEDs 36 shown in FIG. 1 may generate two separate reflections, aligned with axis 52 at different respective positions along the shaft circumference, when all of the LEDs are lit. Alternatively, LEDs 36, or subsets of LEDs 36, may be alternatingly lit in rapid succession (e.g., such that the last LED is lit within 1-100, such as within 5-50, milliseconds of the first LED), such that various different reflections are rapidly generated.

Alternatively or additionally, to vary the shapes and/or positions of the reflections that are imaged, the illumination and/or imaging of the catheter shaft may be conducted from multiple different positions, as described above with reference to FIGS. 2A-C. For example, multiple different light sources and/or imaging devices, disposed at different respective locations, may be used. Alternatively or additionally, a light source and/or imaging device may be moved with respect to the catheter shaft while the images are acquired.

Alternatively or additionally, track 26, and/or a separate jittering mechanism, may jitter the catheter shaft as the catheter shaft passes underneath the inspection system, such that the shape and/or position of the reflection is varied.

Subsequently to receiving the multiple images, the processor compares at least one parameter of the reflection, as exhibited in each of the images, to the parameter as exhibited in the other images. Subsequently, in response to the comparison, the processor may select at least one image, but not the other images, for processing.

One such parameter is the average or median peak-to-peak amplitude of the reflection (i.e., the average or median difference between positive peaks 48 and negative peaks 50), or of the intensity of the reflection. In particular, the processor may select those images showing a greater peak-to-peak amplitude, relative to the other images. This amplitude may be normalized by the sum of the absolute values of the peaks; for example, given a positive peak $A_{max}$ and a negative peak $A_{min}$, the normalized peak-to-peak amplitude may be defined as $(A_{max}-A_{min})/(A_{max}+A_{min})$.

Another such parameter is the energy of the dominant frequency of the reflection or of the intensity of the reflection, relative to other frequencies. For example, the processor may compute an FFT of each of the reflections, and/or of the brightness function B(x) for each of the reflections. For each FFT, the processor may compute the percentage difference between the highest peak of the FFT and the second-highest peak. The processor may then select those images having a greater percentage difference, relative to the other images.

As noted above, the processor may also use the techniques described above to select a reflection from multiple reflections that are shown in a single image.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for inspecting a tubular device that includes an outer surface and a spatially-periodic supporting structure beneath the outer surface, the system comprising:
   (i) an imaging device, configured to capture a set of images, the set of images including every portion of the tubular device, the set of images being configured to acquire a reflection of light from the outer surface; and
   iii) a processor, configured to ascertain a spatial frequency of the supporting structure by processing the set of images.

2. The system according to claim 1, further comprising a light source, configured to illuminate the outer surface with the light so as to generate the reflection.

3. The system according to claim 1, the processor being further configured to, in response to the spatial frequency being different from a target spatial frequency, control a manufacturing of the tubular device so as to bring the spatial frequency into accordance with the target spatial frequency.

4. The system according to claim 1, the supporting structure being selected from the group of supporting structures consisting of: a coil, and a braid.

5. The system according to claim 1, the reflection being shaped to define a sinusoid, and the processor being configured to ascertain the spatial frequency of the supporting structure based on a frequency of the sinusoid.

6. The system according to claim 5, the processor being further configured to, prior to processing the set of images:
compare a parameter of the sinusoid, as exhibited in an image of the set of images, to the parameter as exhibited in another image, and
select the image, but not the other image, for the processing, in response to the comparison.

7. The system according to claim 6, the parameter including a peak-to-peak amplitude of the sinusoid.

8. The system according to claim 6, the parameter including an energy of a dominant frequency of the sinusoid.

9. The system according to claim 1, the spatial frequency of the supporting structure being a first spatial frequency, and the processor being configured to ascertain the first spatial frequency based on a second spatial frequency of an intensity of the reflection.

10. A method, comprising:
(i) using a light source, illuminating an outer surface of a tubular device with light, the tubular device including a spatially-periodic supporting structure, the supporting structure including a braid, beneath the outer surface;
(ii) while illuminating the outer surface, using an imaging device, acquiring an image of a reflection of the light from the outer surface; and
(iii) by processing the image, ascertaining a spatial frequency of the supporting structure.

11. The method according to claim 10, illuminating the outer surface comprising illuminating the outer surface while the tubular device is being manufactured.

12. The method according to claim 11, further comprising, in response to the spatial frequency being different from a target spatial frequency, controlling the manufacturing of the tubular device so as to bring the spatial frequency into accordance with the target spatial frequency.

13. The method according to claim 10, the reflection being shaped to define a sinusoid, and ascertaining the spatial frequency of the supporting structure comprising ascertaining the spatial frequency of the supporting structure based on a frequency of the sinusoid.

14. The method according to claim 13, further comprising, prior to processing the image:
(i) comparing a parameter of the sinusoid, as exhibited in the image, to the parameter as exhibited in another image, and
(ii) selecting the image, but not the other image, for the processing, in response to the comparison.

15. The method according to claim 14, the parameter including a peak-to-peak amplitude of the sinusoid.

16. The method according to claim 14, the parameter including an energy of a dominant frequency of the sinusoid.

17. The method according to claim 13, the supporting structure including at least two coils that are braided with one another, and illuminating the outer surface comprising illuminating the outer surface such that peaks of the sinusoid are located at respective crossings of the coils.

18. The method according to claim 10, the spatial frequency of the supporting structure being a first spatial frequency, and ascertaining the first spatial frequency comprising ascertaining the first spatial frequency based on a second spatial frequency of an intensity of the reflection.

19. A computer software product comprising a tangible non-transitory computer-readable medium in which program instructions are stored, which instructions, when read by a processor, cause the processor to:
(i) receive an image of a reflection of light from an outer surface of a tubular device that includes a spatially-periodic supporting structure, the supporting structure including a braid, beneath the outer surface, and
(ii) ascertain a spatial frequency of the supporting structure by processing the image.

20. The method according to claim 10, further comprising continuously advancing the tubular device a length relative to the light source and repeating the method of claim 10 until every portion of the tubular device has been processed to ascertain the spatial frequency of the supporting device for every portion of the tubular device.

* * * * *